(12) United States Patent
Meadows et al.

(10) Patent No.: US 12,350,238 B2
(45) Date of Patent: Jul. 8, 2025

(54) SYSTEM AND METHOD FOR REAL-TIME HUMIDITY AND TEMPERATURE SENSING TO VERIFY PROPER NASOGASTRIC TUBE PLACEMENT

(71) Applicant: Avent, Inc., Alpharetta, GA (US)

(72) Inventors: Vernon Meadows, Lilburn, GA (US); Preston A. Moeller, Alpharetta, GA (US); Donald McMichael, Roswell, GA (US); Anthony D. Roberts, Canton, GA (US)

(73) Assignee: Avent, Inc., Alpharetta, GA (US)

( * ) Notice: Subject to any disclaimer, the term of this patent is extended or adjusted under 35 U.S.C. 154(b) by 519 days.

(21) Appl. No.: 16/364,362

(22) Filed: Mar. 26, 2019

(65) Prior Publication Data

US 2020/0306141 A1    Oct. 1, 2020

(51) Int. Cl.
*A61J 15/00*   (2006.01)
*A61M 25/00*   (2006.01)
(Continued)

(52) U.S. Cl.
CPC ....... *A61J 15/0088* (2015.05); *A61J 15/0003* (2013.01); *A61J 15/0015* (2013.01);
(Continued)

(58) Field of Classification Search
CPC .......... A61M 25/0026; A61M 25/0028; A61M 25/0097; A61M 2025/0001;
(Continued)

(56) References Cited

U.S. PATENT DOCUMENTS 4,836,214 A   6/1989   Sramek
4,921,481 A   5/1990   Danis et al.
(Continued)

FOREIGN PATENT DOCUMENTS

CN   106 691 866 A   5/2017
WO   WO 92/17150     10/1992
(Continued)

OTHER PUBLICATIONS

Report and Written Opinion for PCT/US2020/022324, dated Jul. 2, 2020, 28 pages.

*Primary Examiner* — Kami A Bosworth
(74) *Attorney, Agent, or Firm* — Meunier Carlin & Curfman LLC

(57) ABSTRACT

A tubing assembly for use in conjunction with electronic catheter guidance systems is provided and includes a catheter and a sensor. The catheter extends in a longitudinal direction and has a proximal end and a distal end that define a lumen therebetween. Further, the catheter is configured for placement within a digestive tract of a patient. The sensor includes a temperature sensor, relative humidity sensor, or both, and can be located within the lumen of the catheter or in an air sampling chamber connected to the catheter. The sensor can communicate with a processor to deliver temperature and/or relative humidity readings to a display device. A constant temperature or relative humidity profile, or both after a pre-determined amount of time can indicate placement of the catheter in the digestive tract. A catheter guidance system and a method for accurately placing a catheter in the digestive tract are also provided.

11 Claims, 14 Drawing Sheets

(51) Int. Cl.
  *A61M 39/10* (2006.01)
  *A61B 5/00* (2006.01)
  *A61M 5/38* (2006.01)
(52) U.S. Cl.
  CPC ........ *A61M 25/0097* (2013.01); *A61M 39/10* (2013.01); *A61B 5/6852* (2013.01); *A61J 15/0065* (2013.01); *A61M 5/385* (2013.01); *A61M 2039/1077* (2013.01)
(58) Field of Classification Search
  CPC .. A61M 2025/0002; A61M 2025/0003; A61M 2025/0166; A61J 15/0003; A61J 15/0015; A61J 15/0065; A61J 15/0073; A61J 15/008; A61J 15/0084; A61J 15/0088; A61J 15/0007; A61J 15/0019; A61J 15/0023; A61J 15/0026; A61B 5/06; A61B 5/061; A61B 5/065; A61B 2562/0271; A61B 2562/029; A61B 2562/0276
  See application file for complete search history.

(56) References Cited

U.S. PATENT DOCUMENTS

| | | | |
|---|---|---|---|
| 5,460,603 A * | 10/1995 | DeSantis | A61J 15/0015 604/323 |
| 6,039,696 A * | 3/2000 | Bell | A61M 16/08 128/204.21 |
| 6,334,064 B1 | 12/2001 | Fiddian-Green | |
| 6,357,447 B1 | 3/2002 | Swanson et al. | |
| 7,818,155 B2 | 10/2010 | Stuebe et al. | |
| 8,147,486 B2 | 4/2012 | Honour et al. | |
| 8,613,702 B2 | 12/2013 | Feer et al. | |
| 8,986,230 B2 | 3/2015 | Nishtala | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,532,739 B2 | 1/2017 | Bennett-Guerrero | |
| 9,610,227 B2 | 4/2017 | Elia | |
| 9,642,779 B2 | 5/2017 | Elia et al. | |
| 9,713,579 B2 * | 7/2017 | Elia | A61B 5/746 |
| 2005/0124935 A1 | 6/2005 | McMichael | |
| 2006/0019327 A1 * | 1/2006 | Brister | A61B 5/14546 435/25 |
| 2006/0173407 A1 * | 8/2006 | Shaughnessy | A61M 25/0105 604/95.01 |
| 2008/0077043 A1 | 3/2008 | Malbrain et al. | |
| 2008/0097179 A1 | 4/2008 | Russo | |
| 2008/0167607 A1 | 7/2008 | Pfeiffer et al. | |
| 2008/0249467 A1 | 10/2008 | Burnett et al. | |
| 2012/0016256 A1 | 1/2012 | Mabary et al. | |
| 2012/0208285 A1 * | 8/2012 | Deighan | A61M 16/04 436/163 |
| 2012/0277619 A1 | 11/2012 | Starkebaum et al. | |
| 2012/0323089 A1 | 12/2012 | Feer et al. | |
| 2013/0046172 A1 * | 2/2013 | Waitzman | A61B 5/06 600/424 |
| 2013/0225946 A1 | 8/2013 | Feer et al. | |
| 2016/0113843 A1 | 4/2016 | Elia et al. | |
| 2016/0129223 A1 | 5/2016 | Kirschenman | |
| 2016/0331298 A1 | 11/2016 | Burnett et al. | |
| 2017/0020396 A1 | 1/2017 | Boone, III et al. | |
| 2017/0071502 A1 | 3/2017 | Bennett-Guerrero | |
| 2017/0202750 A1 | 7/2017 | Elia | |
| 2018/0042819 A1 * | 2/2018 | Succi | A61J 15/0026 |
| 2018/0078195 A1 | 3/2018 | Sutaria et al. | |
| 2018/0117285 A1 | 5/2018 | Shaughnessy et al. | |
| 2018/0161249 A1 | 6/2018 | Elia et al. | |
| 2018/0289536 A1 | 10/2018 | Burnett | |

FOREIGN PATENT DOCUMENTS

| | | |
|---|---|---|
| WO | WO 2017/184843 A1 | 10/2017 |
| WO | WO 2020/069171 A1 | 4/2020 |

* cited by examiner

SYSTEM AND METHOD FOR REAL-TIME HUMIDITY AND TEMPERATURE SENSING TO VERIFY PROPER NASOGASTRIC TUBE PLACEMENT

BACKGROUND OF THE INVENTION

Physicians and other health care providers frequently use catheters to treat patients. Known catheters include a tube which is inserted into the human body. Certain catheters are inserted through the patient's nose or mouth for treating the digestive or gastrointestinal tract. These catheters, sometimes referred to as enteral catheters, typically include feeding tubes. The feeding tube lies in the stomach or intestines, and a feeding bag delivers liquid nutrient, liquid medicine or a combination of the two to the patient.

When using these known catheters, it is important to place the end of the catheter at the proper location within the human body. Erroneous placement of the catheter tip may injure or harm the patient. For example, if the health care provider erroneously places an enteral catheter into the patient's trachea, lungs, or other anatomical regions of the respiratory system rather than through the esophagus and to the stomach to reach the desired location in the digestive tract for delivering nutrients or medicine, liquid may be introduced into the lungs with harmful, and even fatal, consequences. In particular, the esophagus of the digestive tract and the trachea of the respiratory system are in close proximity to each other and are blind to the health care provider during catheter placement, which creates a dangerous risk for erroneous catheter placement.

In some cases, health care providers use X-ray machines to gather information about the location of the catheters within the body. There are several of disadvantages with using X-ray machines. For example, these machines are relatively large and heavy, consume a relatively large amount of energy and may expose the patient to a relatively high degree of radiation. Also, these machines are typically not readily accessible for use because, due to their size, they are usually installed in a special X-ray room. This room can be relatively far away from the patient's room. Therefore, health care providers can find it inconvenient to use these machines for their catheter procedures. In addition, using X-ray technology is expensive and is a time-consuming task that can create unnecessary delays in delivering critical nutrients to the patient.

Accordingly, there is a need to overcome each of these disadvantages.

SUMMARY OF THE INVENTION

Objects and advantages of the invention will be set forth in part in the following description, or may be obvious from the description, or may be learned through practice of the invention.

In one particular embodiment of the present invention a tubing assembly is provided. The tubing assembly includes a catheter having a proximal end and a distal end and extending in a longitudinal direction, where the proximal end and the distal end define a lumen therebetween. Further, the catheter is configured for placement within a digestive tract of a patient. The tubing assembly also includes a sensor, where the sensor includes a temperature sensor, a relative humidity sensor, or a combination thereof.

In one embodiment, the sensor can be located within the lumen of the catheter.

In another embodiment, the tubing assembly can include an air sampling chamber Further, the sensor can be located within the air sampling chamber.

In still another embodiment, the sensor can be configured to provide temperature readings, relative humidity readings, or a combination thereof measured by the sensor from air in the lumen to a processor in real-time. Further, the sensor can be configured for a wired connection or a wireless connection to the processor.

In yet another embodiment, the sensor can be protected from fluid ingress by a porous filter material.

In one more embodiment, the tubing assembly can include a multi-port connector. Further, the multi-port connector can include a nutrient branch and a medicine branch.

In an additional embodiment, the tubing assembly can include a port and an aspiration line connected thereto.

In another particular embodiment of the present invention, a catheter guidance system is provided. The catheter guidance system includes a processor, a power source, a display device, and a tubing assembly. The tubing assembly includes a catheter and a sensor. The catheter has a proximal end and a distal end and extends in a longitudinal direction, where the proximal end and the distal end define a lumen therebetween. Meanwhile, the sensor includes a temperature sensor, a relative humidity sensor, or a combination thereof, where the sensor communicates with the processor via an electrical connection to deliver temperature readings, relative humidity readings, or a combination thereof measured by the sensor from air in the lumen to the processor in real-time. Further, the display device is coupled to the processor and displays the temperature readings, relative humidity readings, or a combination thereof communicated by the sensor. A constant temperature profile, a constant relative humidity profile, or both a constant temperature profile and a constant relative humidity profile after a pre-determined amount of time as shown on the display device indicates placement of the catheter in a digestive tract of a patient.

In another embodiment, the catheter guidance system can include a memory device storing instructions which, when executed by the processor, cause the processor to (i) interpret the temperature readings, the relative humidity readings, or a combination thereof communicated by the sensor and (ii) cause the display device to communicate whether or not the catheter is placed within the digestive tract of the patient based on the interpretation of the temperature readings, the relative humidity readings, or a combination thereof.

In still another embodiment, the sensor can be located within the lumen of the catheter or within an air sampling chamber.

In yet another embodiment, the sensor can be protected from fluid ingress by a porous filter material.

In one more particular embodiment of the present invention, a method for determining if a catheter is placed within a digestive tract of a body of a patient is provided. The method includes: (a) inserting a distal end of a tubing assembly into an orifice of the body, where the tubing assembly includes the catheter, where the catheter has a proximal end and a distal end and extends in a longitudinal direction, where the proximal end and the distal end define a lumen therebetween; and a sensor, where the sensor comprises a temperature sensor, a relative humidity sensor, or a combination thereof; (b) electrically connecting the sensor to a processor via a wired connection or a wireless connection; (c) activating the sensor, where the sensor measures temperature, relative humidity, or a combination thereof from air in the lumen and communicates with the processor via the wired connection or the wireless connection to deliver temperature readings, relative humidity readings, or a combination thereof to the processor in real-time, wherein a display device is coupled to the processor and displays the temperature readings, relative humidity readings, or a combination thereof communicated by the sensor; (d) advancing the distal end of the catheter inside the body in a direction away from the orifice while the sensor is activated; and (e) observing the temperature readings, relative humidity readings, or a combination thereof on the display device, wherein a constant temperature profile, a constant relative humidity profile, or both a constant temperature profile and a constant relative humidity profile after a pre-determined amount of time indicates placement of the catheter in a digestive tract of a patient.

In another embodiment, a memory device stores instructions which, when executed by the processor, cause the processor to (i) interpret the temperature readings, the relative humidity readings, or a combination thereof communicated by the sensor and (ii) cause the display device to communicate whether or not the catheter is placed within the digestive tract of the patient based the interpretation of the temperature readings, the relative humidity readings, or a combination thereof.

In still another embodiment, the orifice can be a nose or a mouth.

In yet another embodiment, the sensor can be located within the lumen of the catheter or within an air sampling chamber.

In one more embodiment, suction from an aspiration system directs air sampled from a distal end of the catheter to the sensor.

In an additional embodiment, the sensor can be protected from fluid ingress by a porous filter material.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
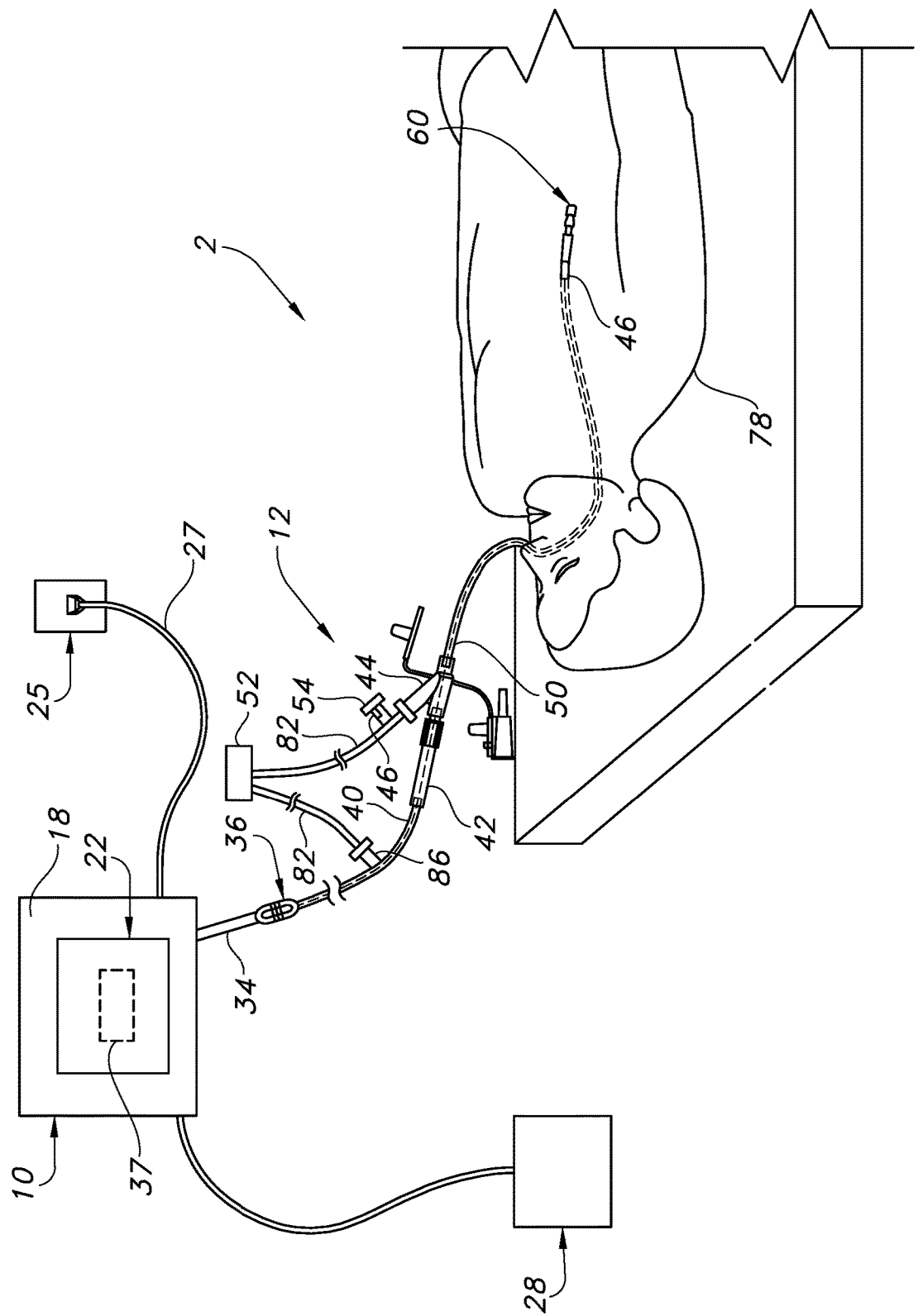
FIG. 1 is a perspective view of the catheter guidance system illustrating the display device, electronic catheter unit and the sensor that is at least temporarily contained with the electronic catheter unit as it is being used to position a catheter within a patient in one embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present invention is directed to a tubing assembly that includes a catheter having a proximal end and a distal end and extending in a longitudinal direction, where the proximal end and the distal end define a lumen therebetween. Further, the catheter is configured for placement within a digestive tract of a patient. The tubing assembly also includes a sensor, where the sensor includes a temperature sensor, a relative humidity sensor, or a combination thereof. The sensor can be located within the lumen of the catheter or in an air sampling chamber connected to the catheter. The sensor can communicate with a processor to deliver temperature and/or relative humidity readings to a display device. A constant temperature or relative humidity profile, or both after a pre-determined amount of time can indicate placement of the catheter in the digestive tract. A catheter guidance system and a method for accurately placing a catheter in the digestive tract are also contemplated by the present invention.

The present inventors have found that the tubing assembly, catheter guidance system, and method described in more detail herein allow for the continuous sampling of air during inspiration and expiration of a patient, where the real-time temperature and/or relative humidity readings measured by the sensor can be used to determine if the distal end of the catheter is accurately placed within the digestive tract (e.g., esophagus, stomach, intestines, etc.) rather than within the respiratory system (e.g., trachea, bronchi, lungs, etc.), where such placement could be harmful and even fatal to a patient. Further, the present inventors have found that because the sensor can obtain measurements and communicate those measurements to processor and ultimately a display device or other communication device (e.g., a phone, pager, etc.) in real time, the correct placement of the catheter can be confirmed within seconds of a catheter placement procedure, which can save valuable time, resources, and cost while at the same time limit patient risk in the event of the erroneous placement of the catheter.

Specifically, the present inventors have found that the real-time monitoring of the temperature and/or relative humidity of the air inside or within a catheter to be placed in a predetermined location along the digestive tract (e.g., esophagus, stomach, intestines, etc.), which is facilitated by the sensor assembly of the catheter guidance system of the present invention, allows for the efficient and accurate placement of the catheter within the digestive tract at a low cost. For instance, the sensor in the tubing assembly can monitor the temperature and/or relative humidity of air within the catheter as it is being directed by a health care provider in to the body of a patient, where the temperature and relative humidity data can be transmitted to a display device via a processor. The health care provider can then view the temperature and relative humidity data to determine if the catheter has been accurately placed in the digestive tract or erroneously placed in an anatomical region of the respiratory system (e.g., the trachea, bronchi, lungs, etc.). Alternatively or additionally, a memory device that can include machine readable instructions and one or more computer programs (which, for example, may include a plurality of algorithms) can be used by the processor to process the data from the sensor, where the display device can then indicate the catheter information to the health care provider in the form of a signal as to whether the catheter is accurately placed in the digestive tract or erroneously placed within, for instance, a portion of the respiratory system. For example, a green check mark or the word "Yes" can be displayed on the screen to indicate accurate placement of the catheter within the digestive or gastrointestinal tract, while a red circle with a diagonal line through it, an "X", or the word "No" can be displayed on the screen for erroneous placement, such as placement within the respiratory system.

The various features of the catheter guidance system are discussed in detail below.

Referring now to the drawings, in an embodiment illustrated in FIGS. 1-4, the catheter guidance system 2 contemplated by the present invention includes: (a) an apparatus 10 having a housing 18 which supports a controller or processor 20 and a display device 22; (b) a power cord 27 that couples the apparatus 10 to a power source 25; (c) a printer 28 coupled to the apparatus 10 for printing out paper having graphics which indicate catheter location information; and (d) an invasive electronic catheter unit 12 in communication with and operatively coupled to the apparatus 10 by a wire, cable, cord or electrical extension 34, which, in turn, is operatively coupled to the processor 20, where the electronic catheter unit 12 includes a tubing assembly 14 that includes a catheter 50 and a sensor 46.

Figure 2:
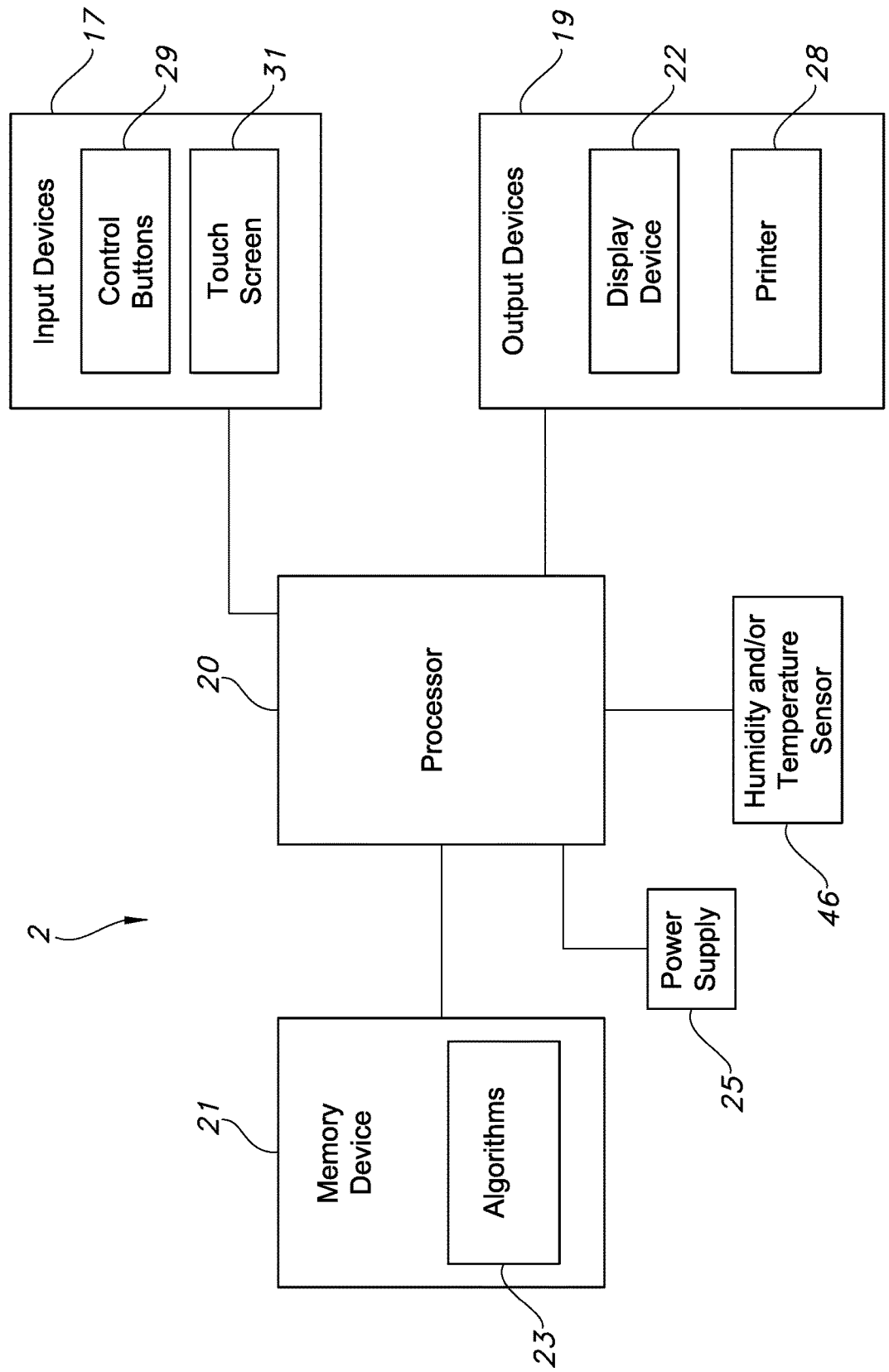
FIG. 2 is schematic block diagram of the electronic configuration of the catheter position guidance system illustrating the processor, memory device, sensor, input devices, and output devices in one embodiment of the present invention.
Figure 3:
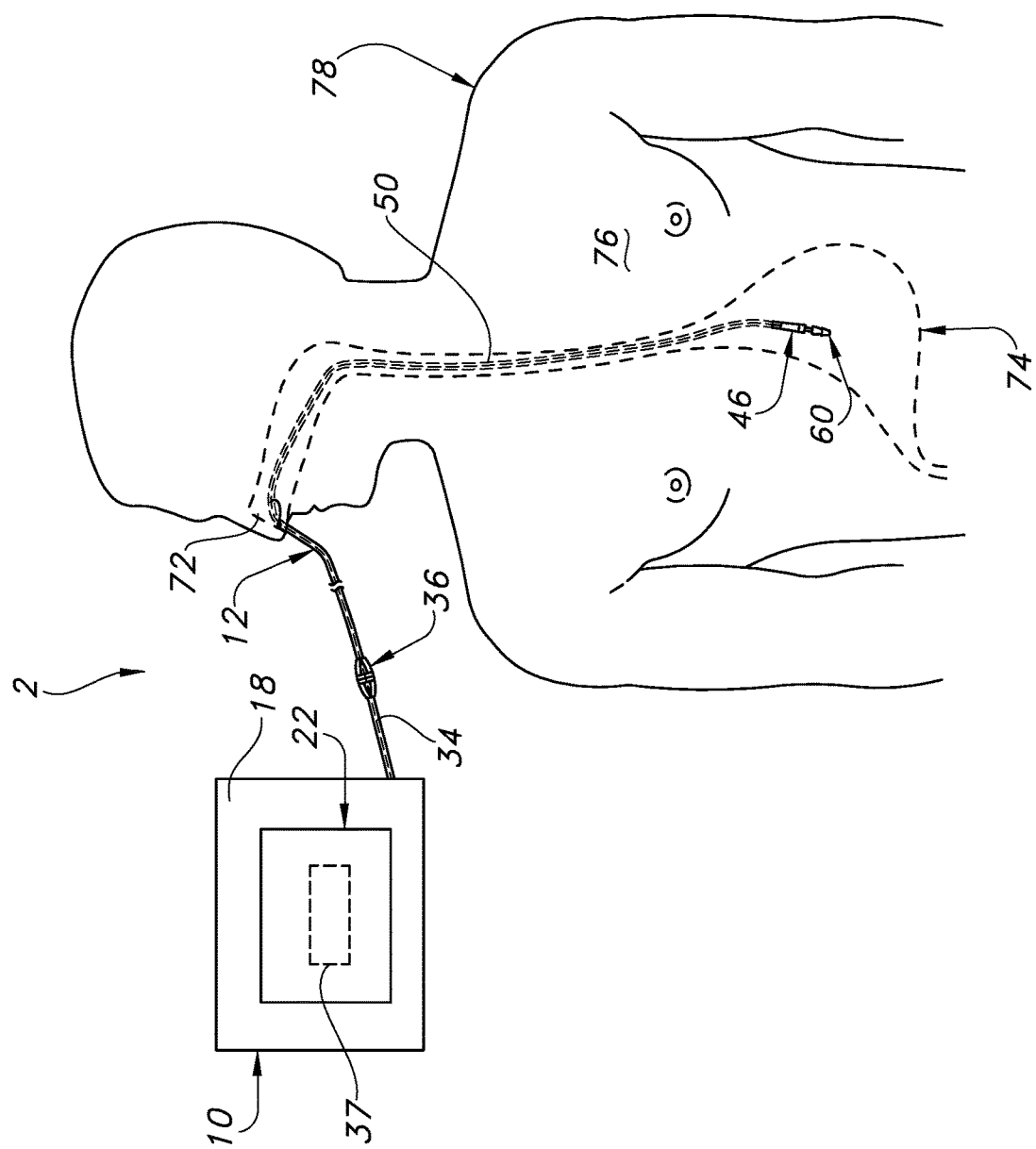
FIG. 3 is a top or plan view of the electronic catheter unit and the display device illustrating an enteral application involving a catheter inserted into a human body and indication of sensor information on the display device.

As best illustrated in FIG. 2, the system 2, in one embodiment, includes: (a) a plurality of input devices 17 for providing input signals to the system 2 such as one or more control buttons 29, a touch screen 31, etc.; (b) a sensor 46 that can continuously measure the temperature and/or relative humidity of air inside or within a catheter 50 of the tubing assembly 14 in real-time; (c) a memory device 21 including machine readable instructions and one or more computer programs (which, for example, may include a plurality of algorithms 23) which are used by the processor 20 to process the signal data produced by the sensor 46; and (d) a plurality of output devices 19 such as the display device 22 and the printer 28 which indicate the catheter information to the health care provider, such as in the form of a graph 37 (see FIGS. 1, 6B-6C, 7B-7C, and 8B-8C. The display device 22 may be any suitable display mechanism including, but not limited to, a liquid crystal display (LCD), light-emitting diode (LED) display, cathode-ray tube display (CRT) or plasma screen.

Figure 4:
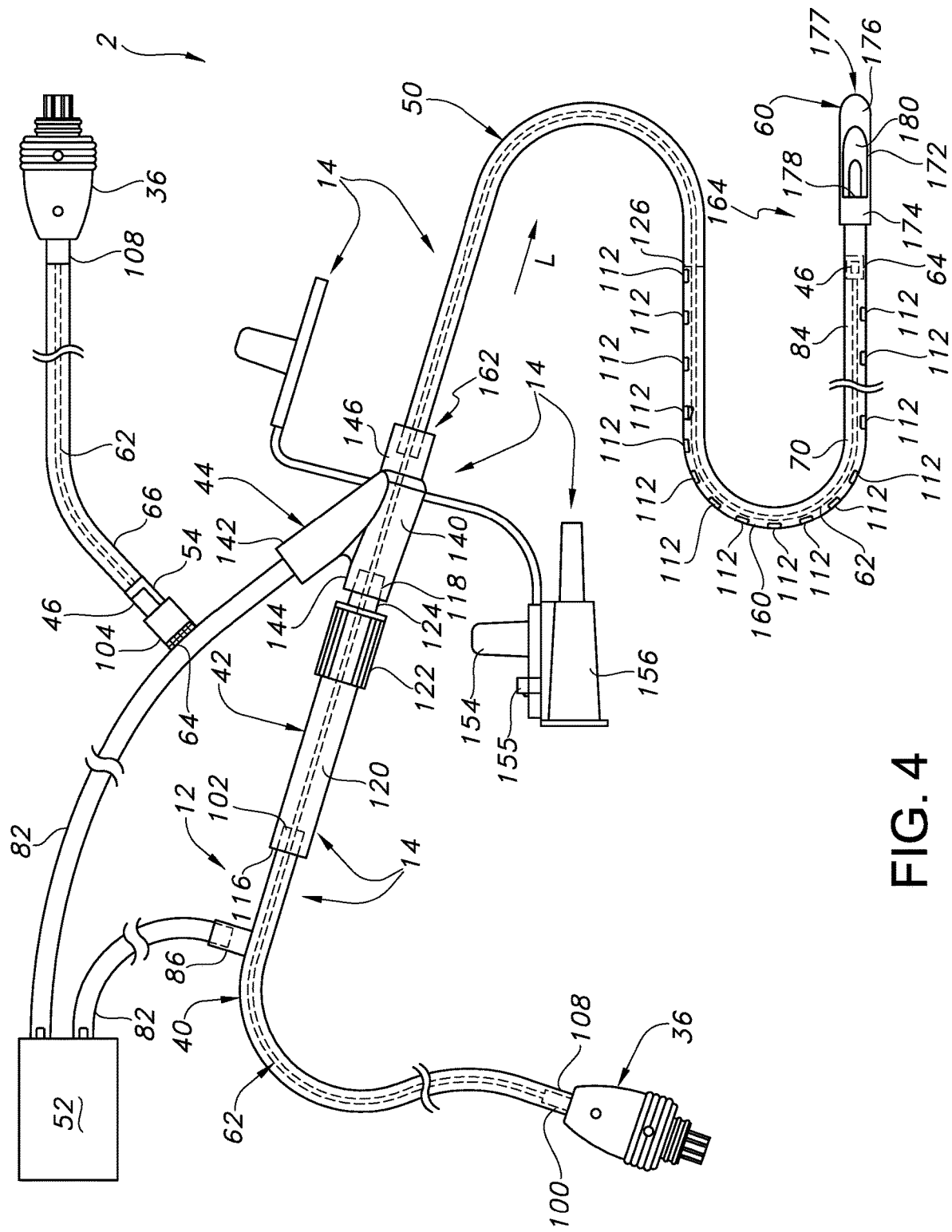
FIG. 4 is a perspective view of the electronic catheter unit illustrating the tubing assembly and the various locations for the sensor and aspiration line according to various embodiments of the present invention.

Health care providers can use the system 2 in a variety of catheter applications. In one example illustrated in FIG. 3, the system 2 is used in an enteral application. Here, a portion 70 of the electronic catheter unit 12 is placed through an orifice 72 of the patient, such as the patient's nose or mouth. The distal end or tip 60 of the electronic catheter unit 12 can ultimately by positioned in the stomach 74. As the health care provider advances the catheter 50 of the electronic catheter unit 12 towards the patient's stomach, the sensor 46 can continuously monitor the temperature and/or relative humidity of the air within the catheter 50 whether the sensor 46 is placed at a distal end or tip 60 of the catheter or more upstream, such as an air sampling chamber 54 as shown in FIGS. 1 and 4. The display device 22 and the printer 28 can indicate information related to the location of the portion 70 of the electronic catheter unit 12 within the body 78, as well as information related to the shape of the pathway taken by the catheter unit 12. It should be appreciated that the system 2 need not indicate the exact location or path of the catheter unit 12 to provide assistance to the health care provider.

Referring to FIG. 4, in one embodiment, the electronic catheter unit 12 includes a tubing assembly 14, which includes the catheter 50 and the sensor 46 of the present invention, where the catheter 50 can generally extend in the longitudinal direction L. In one embodiment, the sensor 46 can be disposed within the lumen 70 of the catheter 50 at a distal end or tip 60 of the catheter 50, as shown in FIG. 4. However, it is also to be understood that the sensor 46 can be located anywhere along the length of the catheter 50. In another embodiment, the electronic catheter unit 12 can include a sample chamber 54 that can alternatively house the sensor 46.

Figure 5:
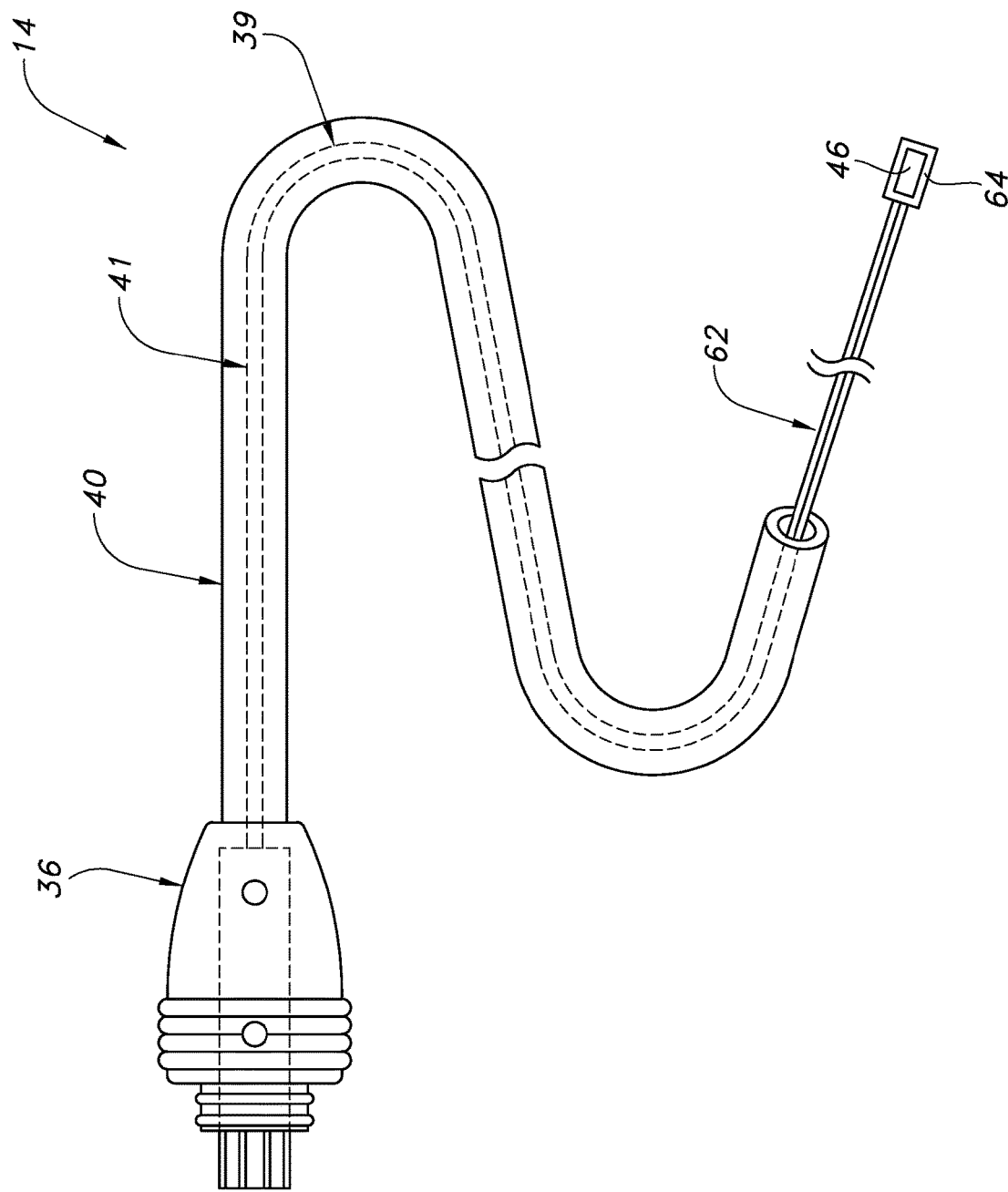
FIG. 5 is a perspective view of the sensor assembly portion of the electronic catheter unit according to one embodiment of the present invention.

As best illustrated in FIGS. 4-5, in one embodiment, such as when a wired connection (as opposed to a wireless connection, which is also contemplated by the present invention, where the sensor 46 includes a battery or other source of power) electrically connects the sensor 46 to the processor 20, the tubing assembly 14 can include (a) a tube or an electrical tubular insulator 40; (b) a mid-connector or union device 42 which receives the tubular insulator 40; (c) a multi-port connector or y-port connector 44 attachable to the union device 42; (d) a catheter 50, such as a feeding tube, connected to the y-port connector 44; and (e) the distal end or tip 60 of the catheter 50, where the sensor 46 can be located within the lumen 70 of the catheter 50 at the distal end or tip 60 or anywhere upstream along the length of the catheter 50.

In one embodiment, the tubular insulator 40 includes a tube having a proximal end 100 attachable to an attachment member or neck 108 of a controller coupler or electrical connector 36 and a distal end 102 receivable by the union device 42; and an internal diameter which is substantially equal to or greater than an external diameter of a wire assembly 62 described below, which can serve as the hard wired electrical connection between the sensor 46 and the processor 20, so as to slide over the wire assembly 62. In another embodiment, the tubular insulator 40 may fit relatively tightly over the wire assembly 62 so as to be secured to the wire assembly 62.

As best illustrated in FIG. 4, in one embodiment, the union device 42 includes: (a) a proximal end 116; (b) a distal end 118; (c) a position adjuster, extender or elongated neck 120 positioned between the proximal end 116 and the distal end 118; (d) a grasp or gripping member 122 positioned adjacent to the distal end 118 so as to assist users in grasping and manipulating the union device 42; and (e) an insert 124 positioned adjacent to the gripping member 122 which is received by the y-port connector 44. When assembled, the proximal end 116 of the union device 42 is coupled to the distal end 102 of the tubular insulator 40.

In one embodiment, the multi-port or y-port connector 44 includes: (a) a body 140; (b) a liquid delivery branch, medicine delivery branch or medicine branch 142 attached to the body 140 for distributing drugs, medicine or other medicinal liquids to the patient; (c) a nutrient delivery branch or feeding branch 144 attached to the body 140 and sized to receive the insert 124 of the union device 42; (d) a catheter or feeding tube connection branch 146 attached to the catheter 50; (e) a flexible or movable arm 148 attached to the body 140; and (f) a flexible or moveable arm 150 attached to the body 140. In an alternative embodiment, y-port connector 44 includes additional branches for administering various nutrients or medicines to the body 78. In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener 155 which secures a tube-size adapter 156 to the arm 150. The tube-size adapter 156 enables fluid delivery tubes (not shown) having various diameters to connect to the feeding branch 144 of the y-port connector 44.

As illustrated in FIG. 4, in one embodiment, the catheter 50 includes a feeding tube or catheter 50 with a body 160 having a proximal end 162 attached to the catheter connection branch 146 of the y-port connector 44 and a distal end 164. The proximal end 162 is insertable into the catheter connection branch 146 of the y-port connector 44 so as to bring the catheter 50 into fluid communication with the y-port connector 44. As also shown in FIG. 4, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body while decreasing the likelihood that the opening 180 will become clogged.

The tubular connector 40, union device 42, y-port connector 44, catheter 50, and tip 60 can be made from any suitable polymer or plastic material including, but not limited to, polyamide, polyethylene, polypropylene, polyurethane, silicone and polyacrylonitrile.

Referring still to FIGS. 1 and 4, in some embodiments, the tubing assembly 14 can include one or more aspiration lines 82 that can be connected to an aspiration device 52 (e.g., central hospital suction line, a vacuum pump, etc.) that can help in drawing air through the catheter 50 so that the sensor 46 can be exposed to a continuous flow of air for measuring the temperature and/or relative humidity of the sample of air in real-time. One possible location for aspiration line 82 can be connected to the tubular insulator 40 via a port 86. The aspiration line 82 can be connected to the tubular insulator 40 when the sensor 46 is located within the lumen 70 of the catheter and when the sensor 46 is electrically connected to the processor 20 via the electrical connection in the form of a wire assembly 62 that runs through the tubular insulator 40 described above to an electrical connector or controller coupler 36, discussed in more detail below. This arrangement can also be used when the electrical connection from the sensor 46 to the processor 20 is wireless.

Another possible location for the aspiration line 82 can be attached to the delivery branch or medicine branch 142 of the multi-port connector or y-port connector 44, such as when the sensor 46 is located in an air sampling chamber 54 rather than the lumen 70 of the catheter. In such an arrangement, the air sampling chamber 54 can be connected to the aspiration line 82 via a connector 104, where the sensor is then electrically connected to the processor 20 via the wire assembly 62 that extends through the air sampling chamber 54 and through tubing 66 to the electrical connector or controller coupler 36. This arrangement can also be used when the electrical connection from the sensor 46 to the processor 20 is wireless.

Turning now to the specifics of the sensor 46 and referring to FIGS. 1, 4, and 5, a controller coupler or an electrical connector 36 can be operatively connected to the electrical extension 34 and an elongated wire assembly 62 can be operatively coupled to the connector 36 to form a wired connection between the sensor 46 and the processor 20, although it is to be understood that the electrical connection between the processor 20 and the sensor 46 can also be wireless provided that the sensor 46 has its own power source, such as a battery. Further, a wire or elongated stiffener 39 can be attached to the connector 36 and can serve as a support for the wire assembly 62 when it is inserted into the body 160 of the catheter or the tubing 66. Further, the tubular insulator 40 described above can cover a portion 41 of the wire assembly 62 positioned adjacent to the connector 36 in the embodiment where the sensor 46 is positioned within the lumen 70 of the catheter 50. In any event, the electrical connector or controller coupler 36 can provide the electrical connection between the apparatus 10 and the sensor 46 when the sensor 46 is hard wired to the catheter guidance system 2 via the wire assembly 62, regardless of whether the sensor 46 is positioned within the lumen 70 of the catheter or within the air sampling chamber 54.

When the sensor 46 is disposed within the lumen 70 of the catheter 50, the sensor 46 can be surrounded by a filter 64 formed from a porous filter material or porous filter media in order to prevent moisture from the opening 180 in the tip 60 of the catheter 50 from contacting the sensor 46 and affecting its temperature and/or relative humidity readings. For instance, the filter 64 can prevent water or other fluid ingress that may enter through the opening 180 from contacting the sensor 46, while still allowing humid air to penetrate into the lumen 70. Likewise, when the sensor 46 is located in a separate air sampling chamber 54, the filter 64 can be disposed between the sensor 46 and the tip 60 of the catheter 50 to prevent water or other fluid ingress that may enter through the opening 180 from contacting the sensor 46, while still allowing humid air to penetrate into the air sampling chamber 54. In any event, the filter 64 is positioned within the tubing assembly 14 to protect the sensor 46 from water or other fluid ingress that may damage the sensor 46 of affect the accuracy of its temperature and/or relative humidity readings.

Turning now to the makeup of the filter 64, the filter 64 contemplated by the present invention can allow gases but not liquids to pass therethrough. Stated alternately, the filter 64 of the present invention can be vapor permeable and liquid impermeable. The filter 64 may comprise any suitable material or combination thereof. Exemplary suitable materials for the filter 64 include but are not limited to reticulated polymer foams, expanded polymers (such as Porex® expanded polymers available from Porex Corporation, having offices in Fairburn, Ga.), expanded PTFE (such as Gore-Tex® expanded PTFE available from W.L. Gore & Associates, Inc., having offices in Newark, Del.), and porous metals (or powdered metals). As will be appreciated, the rate at which the gases are allowed to pass through the filter 64 is not critical so long as it is sufficient to allow for a sufficient volume of air to come into contact with the sensor 46 to obtain accurate temperature and/or relative humidity readings. It will also be appreciated that air flow rate may be affected or controlled in part by the composition of the filter 64. Nevertheless, in most embodiments, it is generally desirable for the insert to be able to allow at least 3 liters to 5 liters of gas to pass therethrough per hour. For use with a pediatric catheter, it may be desirable for the filter 64 in an appropriately sized adapter to be able to allow at least 1 liter to 2 liters of gas to pass therethrough per hour. Further, it will be appreciated that the filter 64 may be hydrophobic or hydrophilic, although it is desired that the insert or insert media be generally hydrophobic. Where the filter 64 is or contains a hydrophobic filter media or where the filter media is at least in part hydrophobically treated, the filter media may have larger pore sizes and therefore a higher flow rate therethrough (as compared to a hydrophilic or hydrophilically treated media) as the filter 64 will be less likely to absorb liquids, become saturated and allow liquid to pass therethrough.

Additionally, although any suitable sensor 46 for measuring temperature and/or relative humidity that can withstand the environmental conditions of the body can be used in the catheter guidance system 2 of the present invention, in one particular embodiment, the sensor 46 can be in the form of a flip chip package having a small footprint such that it can be placed within the lumen 70 of the catheter 50, the air sampling chamber 54, or any other suitable location within the tubing assembly 14. For instance, the sensor 46 can be a digital temperature and humidity sensor that can include a bandgap temperature sensor and a capacitive humidity sensor that includes analog and digital signal processing, an A/D converter, calibration data memory, and a digital communication interface for communication with the processor 20, all of which combine to allow for real-time, continuous, and highly accurate temperature and humidity sensing (e.g., ±0.3° C. and ±3% relative humidity accuracy). The sensor 46 can measure temperatures ranging from about −30° C. to about 100° C. and relative humidity levels ranging from about 0% relative humidity to about 100% relative humidity and thus can measure relative the temperatures and relative humidity levels to which the catheter 50 might possible be exposed in the body (e.g., about 15° C. to about 40° C. and about 50% relative humidity to about 100% relative humidity and any ranges therebetween). In addition, the sensor 46 can also have a low operation voltage of less than 2.5 volts, such as from about 0.5 volts to about 2 volts, such as from about 1 volt to about 1.9 volts, such as about 1.8 volts, which allows for low power consumption, which can allow for the sensor 46 to be suitable for applications where the electrical connection between the sensor 46 and the processor 20 is wireless as opposed to a wired connection via the wire assembly 62, although a wired connection between the sensor 46 and the process 20 via the electrical connector or controller coupler 36 is still possible. In one particular embodiment, the sensor can be the SHTW2 sensor available from SENSIRON having a foot print of 1.3 millimeters by 0.7 millimeters by 0.5 millimeters.

Figure 6A:
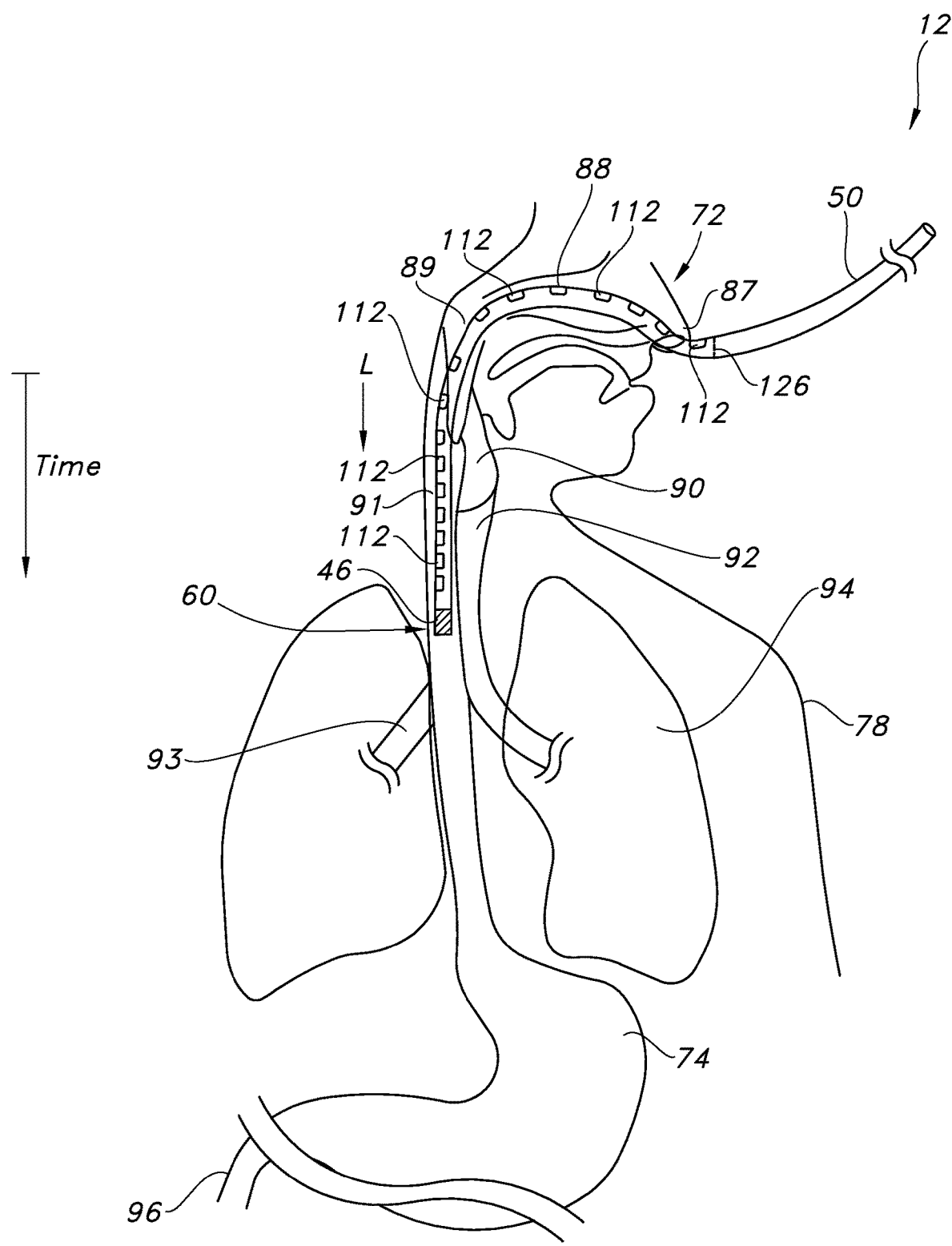
FIG. 6A is a top or plan view of a portion of the electronic catheter unit illustrating an enteral application involving insertion of a catheter into the esophagus of a patient, where the anatomical location of the catheter within the body can be monitored or traced via the sensor assembly of the present invention.

Further, in one embodiment and referring to FIGS. 4 and 6A, the catheter body 160 can have a plurality of markings 112 uniformly spaced along its external surface that can be used in conjunction with the sensor 46 to determine accurate placement of the catheter 50. These markings 112 can function as placement markers which assist the user in assessing the depth that the catheter 50 is placed within the body 78. For instance, when the sensor 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the user can be alerted to start looking for a constant temperature and/or relative humidity as measured by the sensor 46. If the temperature and/or relative humidity readings are still oscillating to the analog of breathing once the markings 112 are no longer visible outside the body 78, then the user will be able to determine that the catheter 50 has been improperly inserted into the trachea 92 instead of the esophagus 91, and the catheter 50 should be immediately retracted. In an alternative embodiment, these markings 112 can assist the user in measuring the flow or distribution of liquid to or from the patient.

Now that the specific components of the catheter guidance system 2 have been discussed in detail, a method of using the catheter guidance system 2 of the present invention in order to verify the accurate placement of a catheter 50 used for enteral feeding in the digestive tract is discussed in more detail below with reference to FIGS. 6A-8C.

Generally, the method for determining if the catheter 50 is accurately placed within a digestive tract of a body 78 of a patient includes inserting a distal end of the tubing assembly 14 (e.g., the distal end or tip 60 of the catheter 50) into an orifice 72 of the body 78, such as a nostril 87 of the patient's nose. As described above, the tubing assembly 14 can include the catheter 50 and the sensor 46. Once the tubing assembly 14 is inserted into the orifice 72 of the body 78, the sensor 46 can be electrically connected to a process 20 via a wired connection, such as the wire assembly 62, although a wireless connection is also contemplated by the present invention such that no wire assembly 62 or controller coupler 62 is required).

Next, the sensor 46 is activated, such as by providing power to the sensor 46, and the sensor 46 then begins to continuously measure the temperature, relative humidity, or a combination thereof from air in the lumen 70 of the catheter and communicates with the processor 20 via the wired connection (e.g., wire assembly 62) or the wireless connection to deliver temperature readings, relative humidity readings, or a combination thereof to the processor 20 in real-time.

In addition, a display device 22 is coupled to the processor 20 and displays the temperature readings, relative humidity readings, or a combination thereof communicated by the sensor 46 for a health care provider to use during the catheter insertion procedure. For instance, as the distal end or tip 60 of the catheter 50 is advanced inside the body 78 in a direction away from the orifice 72 while the sensor 46 is activated, the temperature readings, relative humidity readings, or a combination thereof are observed or monitored on the display device 22.

Specifically, a constant temperature profile, a constant relative humidity profile, or both a constant temperature profile and a constant relative humidity profile displayed or otherwise communicated by the display device 22 after a pre-determined amount of time indicates placement of the catheter 50 in a digestive tract (e.g., esophagus 91, stomach 74, intestine 96, or other anatomical region of the digestive tract of a patient. On the other hand, a non-constant or variable (e.g., sinusoidal wave, square wave, etc.) profile displayed or otherwise communicated by the display device 22 after a pre-determined amount of time indicates placement of the catheter 50 in the respiratory system (e.g., trachea 92, bronchi 93, lungs 94, or other anatomical region of the digestive tract of the patient), at which time the insertion procedure should be stopped immediately and the tubing assembly 14 be removed from the respiratory tract to avoid potential harm to the patient. Further, in order for such information to be displayed or otherwise communicated by the display device 22, a memory device 21 stores instructions which, when executed by the processor 20, cause the processor 20 to (i) interpret the temperature readings, the relative humidity readings, or a combination thereof communicated by the sensor 46 and (ii) cause the display device 22 to communicate whether or not the catheter 50 is placed within the digestive tract of the patient based on the interpretation of the temperature readings, the relative humidity readings, or a combination thereof.

The present inventors have found that the distinctions between the temperature and/or relative humidity profiles of air sampled from the lumen 70 of the catheter, either via placement of the sensor 46 in the lumen 70 of the catheter 50 itself or placement of the sensor 46 in an air sampling chamber upstream, where the air sampled is obtained from the lumen 70 via suction from an aspiration device 52, when the distal end or tip 60 of the catheter 50 is placed within the digestive tract or respiratory system are allow for an efficient and possibly life-saving determination of accurate enteral feeding catheter 50 placement in the digestive tract, where erroneously placing the catheter in the respiratory system would deliver fluid into the lungs, which can have fatal consequences.

Figure 6B:
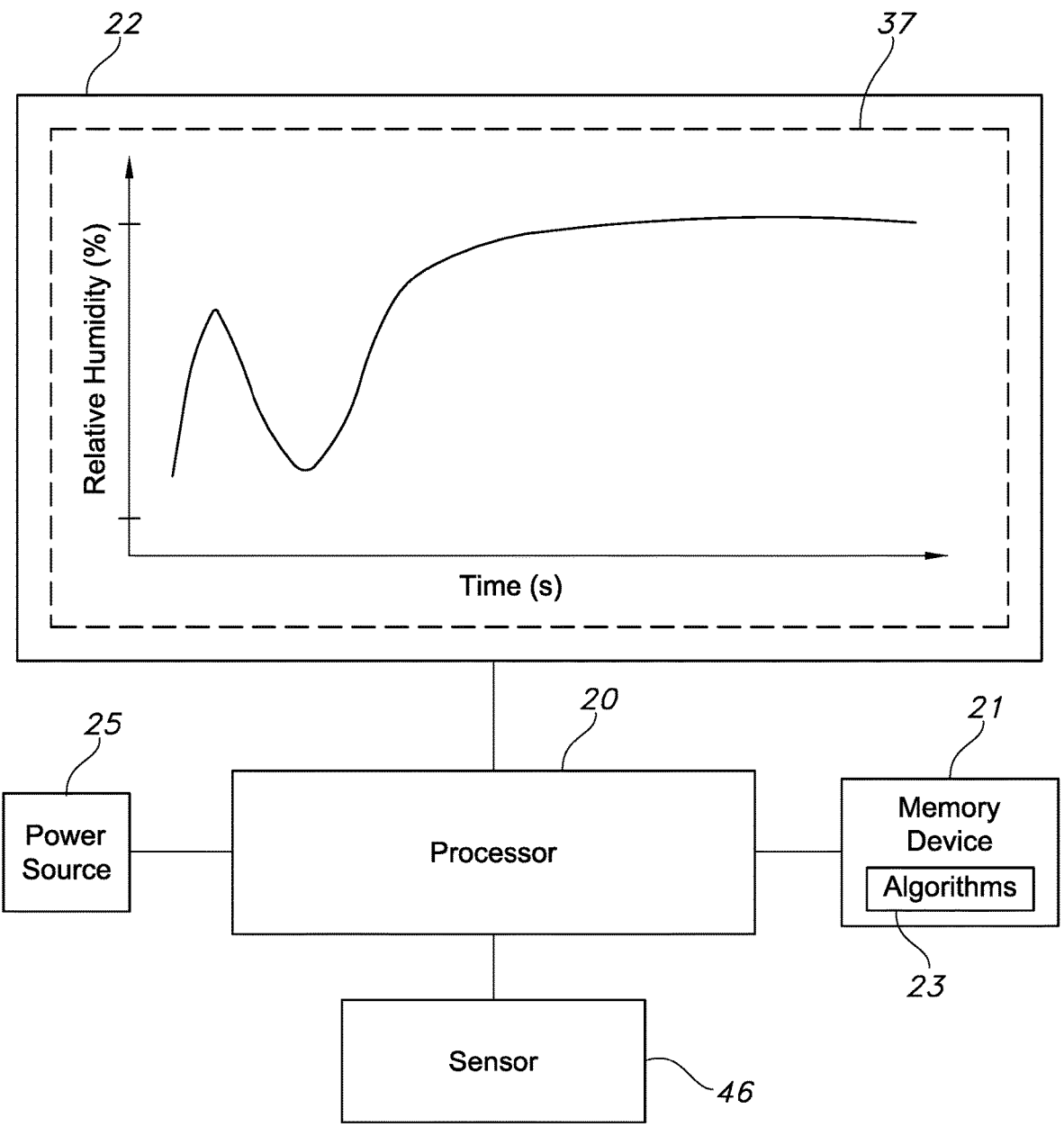
FIG. 6B is a schematic view of the catheter guidance system of the present invention as the system measures the relative humidity of air sampled from the catheter of FIG. 6A in real-time via the sensor assembly.
Figure 6C:
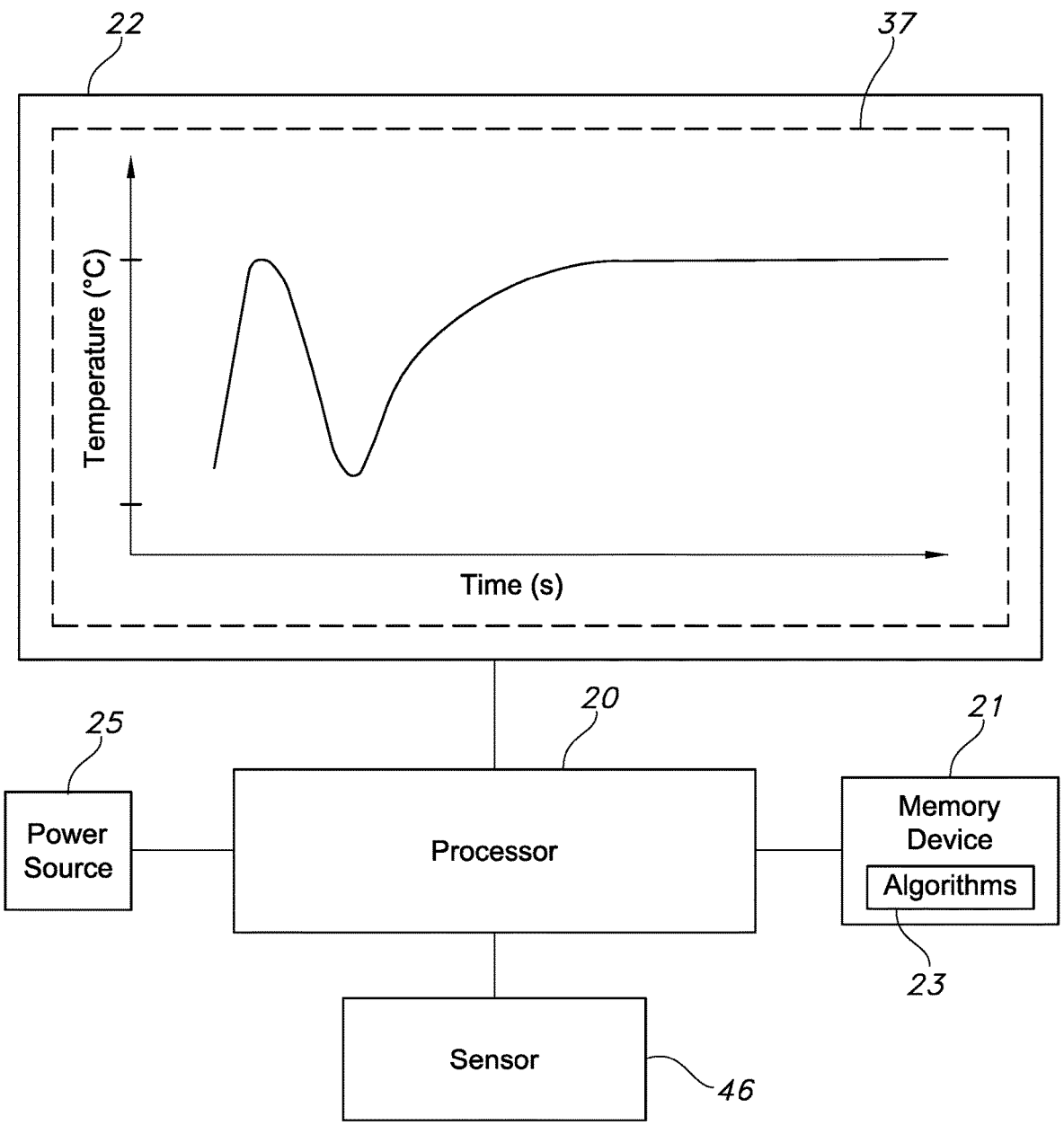
FIG. 6C is a schematic view of the catheter guidance system of the present invention as the system measures the temperature of air sampled from the catheter of FIG. 6A in real-time via the sensor assembly.

For instance, as shown in FIGS. 6A, 6B, and 6C, when the distal end or tip 60 of the catheter 50 is inserted into the nostril 87 of the patient and is advanced through the nasal cavity 88, past the nasopharynx 89, and into the esophagus 91 just past the epiglottis 90, as the sensor 46 is continuously sampling air from the lumen of the catheter 50 over time in seconds (whether the sensor 46 is in the lumen 80 of the catheter 50 itself or in an air sampling chamber 54 as shown in FIGS. 1 and 4), the relative humidity (FIG. 6B) and temperature (FIG. 6C) graphs displayed or otherwise communicated by the processor 20, such as via the display device 22, may initially show non-constant readings, but ultimately reach a constant level over time as the distal end or tip 60 of the catheter 50 travels into the digestive tract and not into the respiratory system. With insertion of the catheter 50 accurately into the digestive tract, the constant readings are ultimately obtained within a matter of seconds of the insertion procedure once the distal end or tip 60 reaches the esophagus 91 and is not exposed to the pattern of breathing associated with inspiration and expiration, where the temperature and relative humidity levels rise and fall in a repetitive pattern.

Figure 7A:
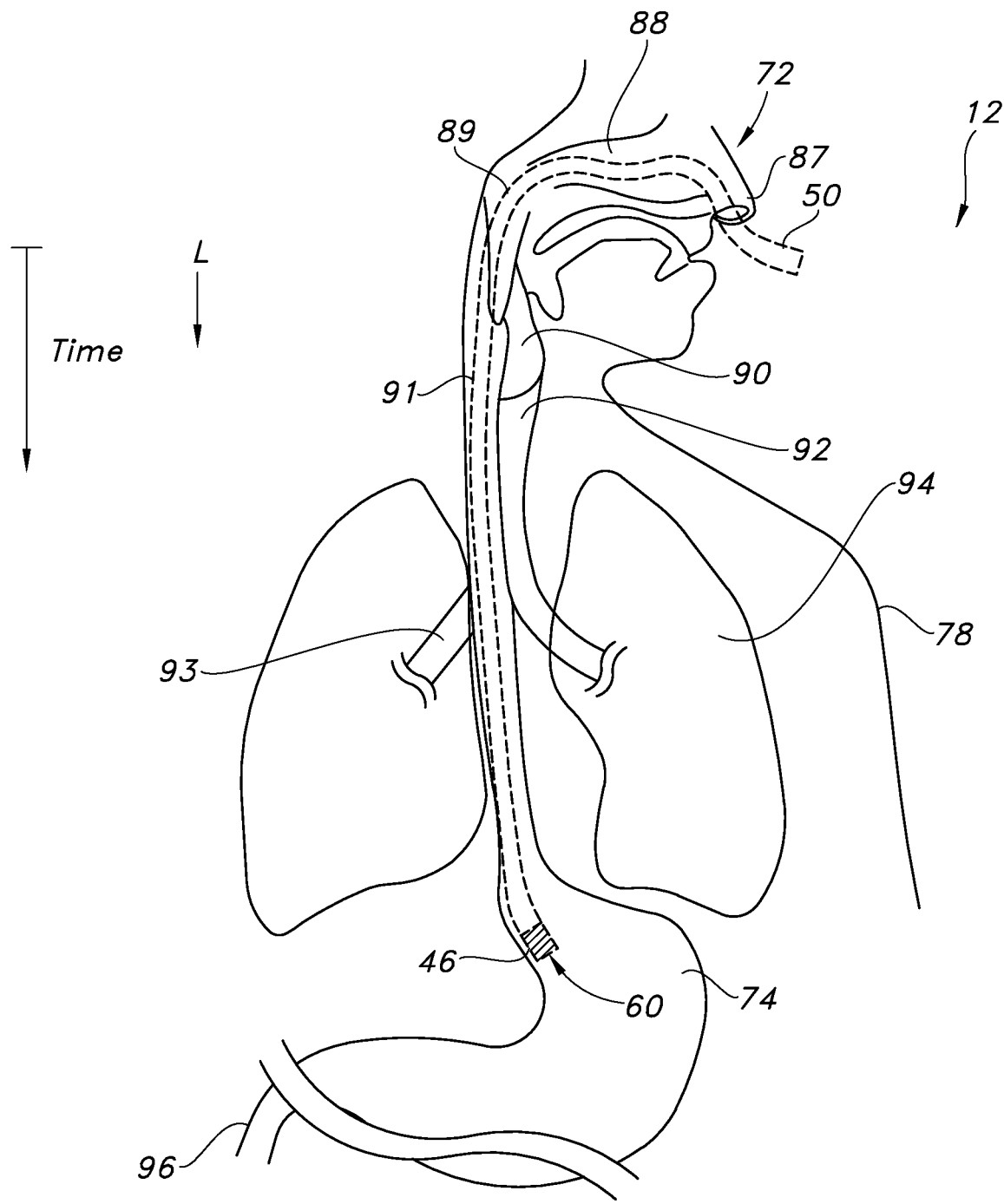
FIG. 7A is a top or plan view of a portion of the electronic catheter unit illustrating an enteral application involving insertion of a catheter into the stomach of a patient, where the anatomical location of the catheter within the body can be monitored or traced via the sensor assembly of the present invention.
Figure 7B:
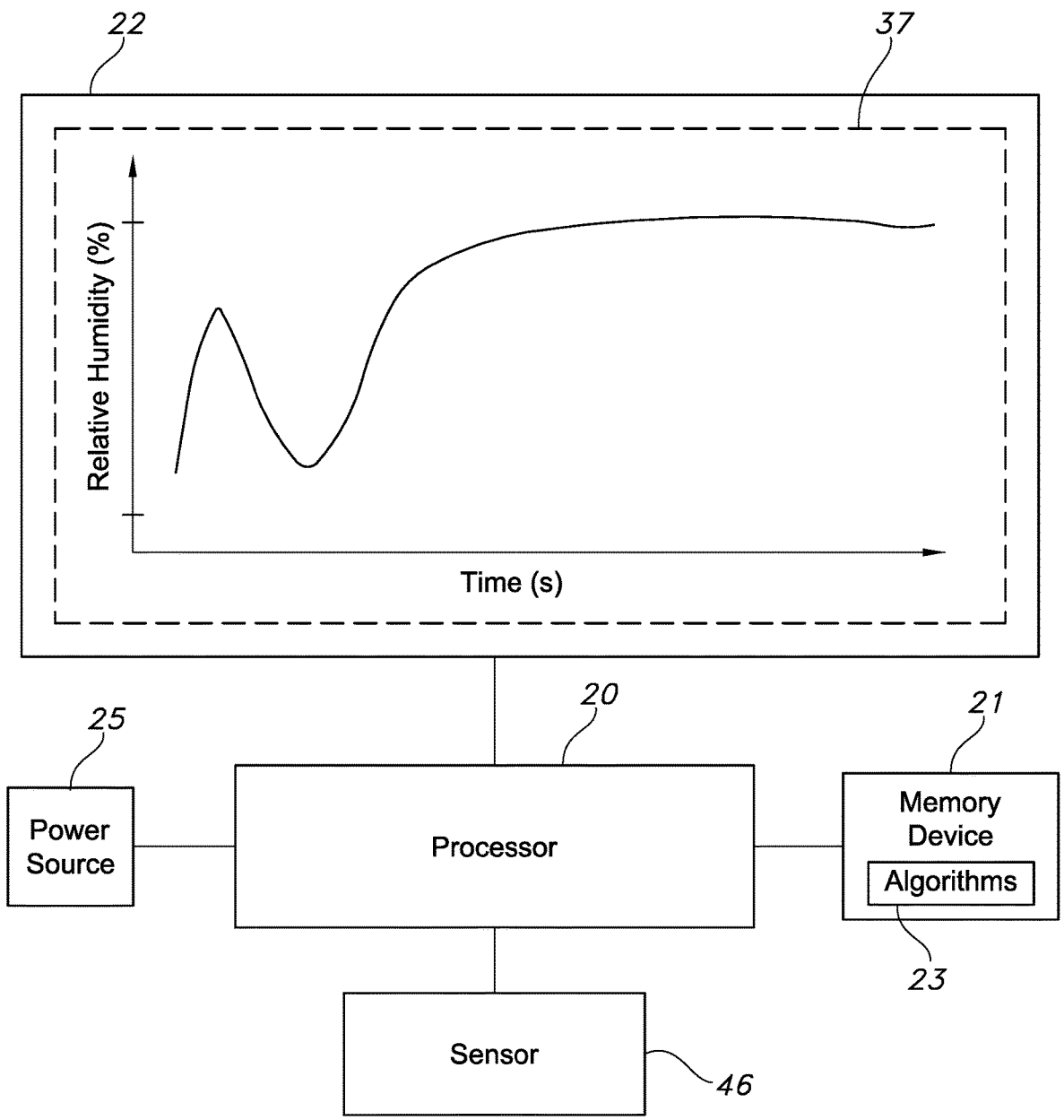
FIG. 7B is a schematic view of the catheter guidance system of the present invention as the system measures the relative humidity of air sampled from the catheter of FIG. 7A in real-time via the sensor assembly.
Figure 7C:
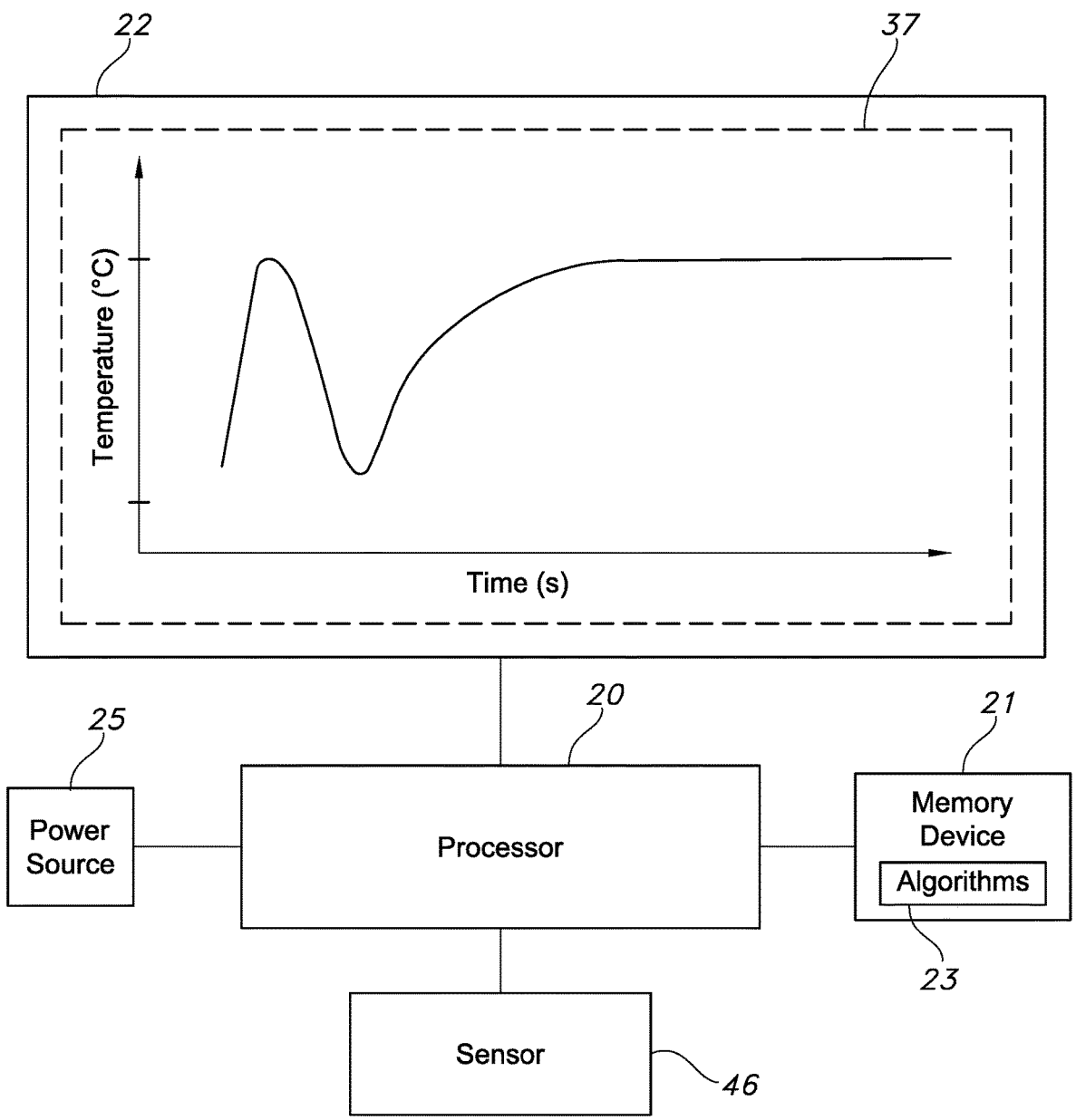
FIG. 7C is a schematic view of the catheter guidance system of the present invention as the system measures the temperature of air sampled from the catheter of FIG. 7A in real-time via the sensor assembly.

Likewise, as shown in FIGS. 7A, 7B, and 7C, when the distal end or tip 60 of the catheter 50 is inserted into the nostril 87 of the patient and is advanced through the nasal cavity 88, past the nasopharynx 89, and into the esophagus 91 just past the epiglottis 90, and then into the stomach 74, as the sensor 46 is continuously sampling air from the lumen of the catheter 50 over time in seconds (whether the sensor 46 is in the lumen 80 of the catheter 50 itself or in an air sampling chamber 54 as shown in FIGS. 1 and 4), the relative humidity (FIG. 7B) and temperature (FIG. 7C) graphs displayed or otherwise communicated by the processor 20, such as via the display device 22, may initially show non-constant readings, but ultimately reach a constant level over time as the distal end or tip 60 of the catheter 50 travels into the digestive tract and not into the respiratory system. With insertion of the catheter 50 accurately into the digestive tract, the constant readings are ultimately obtained within a matter of seconds of the insertion procedure once the distal end or tip 60 reaches the esophagus 91 then the stomach 74 and is not exposed to the pattern of breathing associated with inspiration and expiration, where the temperature and relative humidity levels rise and fall in a repetitive pattern.

Figure 8A:
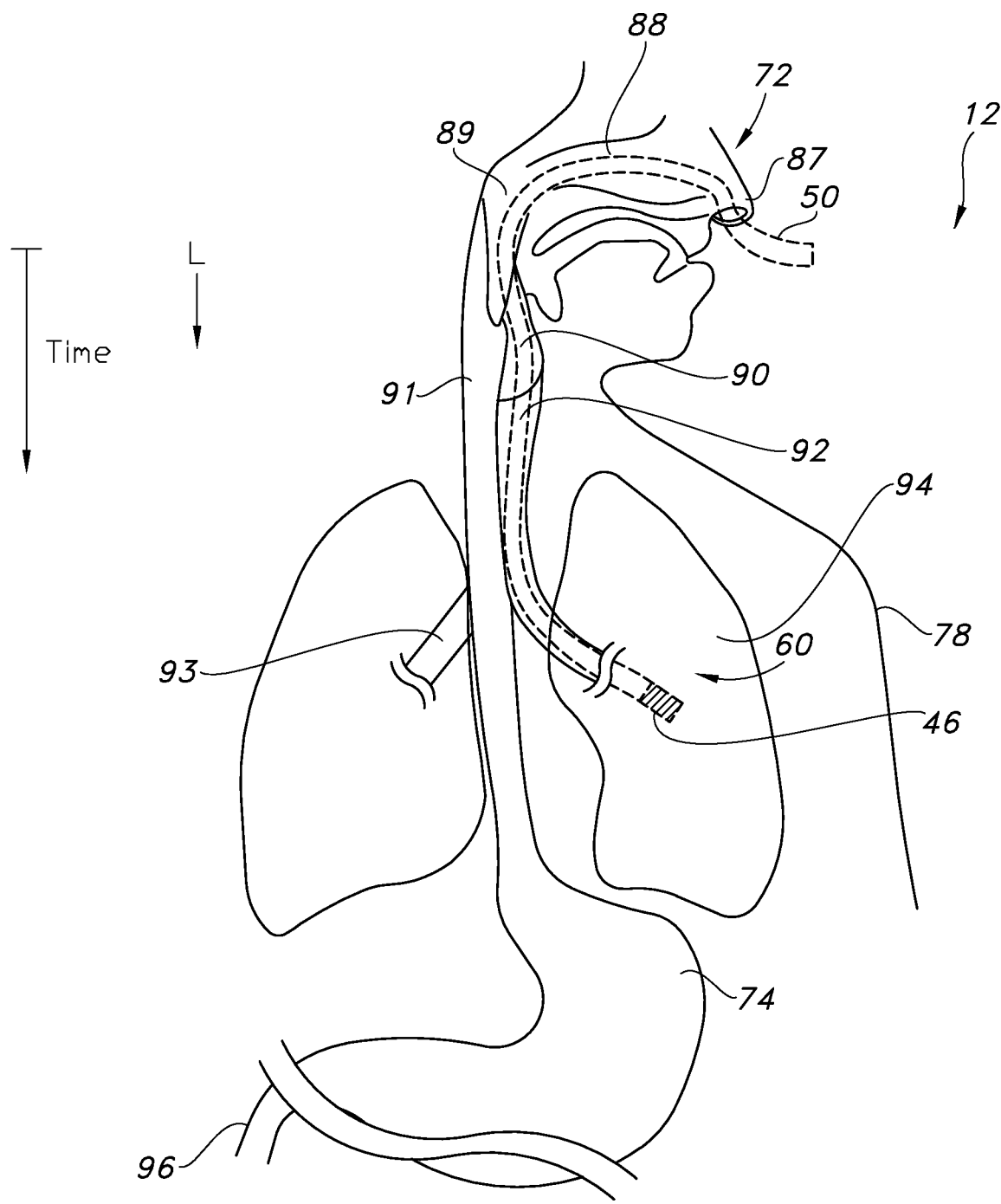
FIG. 8A is a top or plan view of a portion of the electronic catheter unit illustrating an enteral application involving insertion of a catheter erroneously into the lung of a patient, where the anatomical location of the catheter within the body can be monitored or traced via the sensor assembly of the present invention.
Figure 8B:
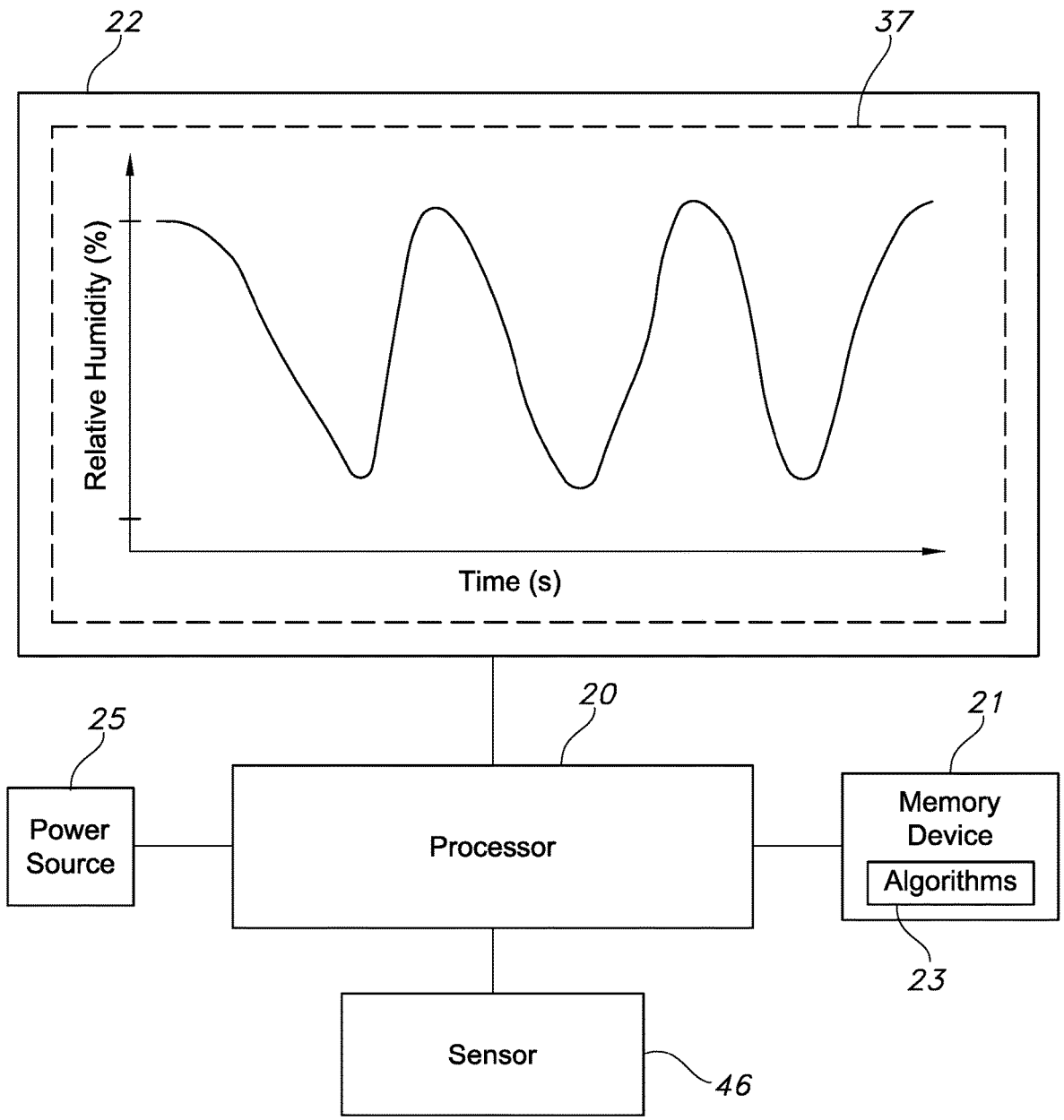
FIG. 8B is a schematic view of the catheter guidance system of the present invention as the system measures the relative humidity of air sampled from the catheter of FIG. 8A in real-time via the sensor assembly.
Figure 8C:
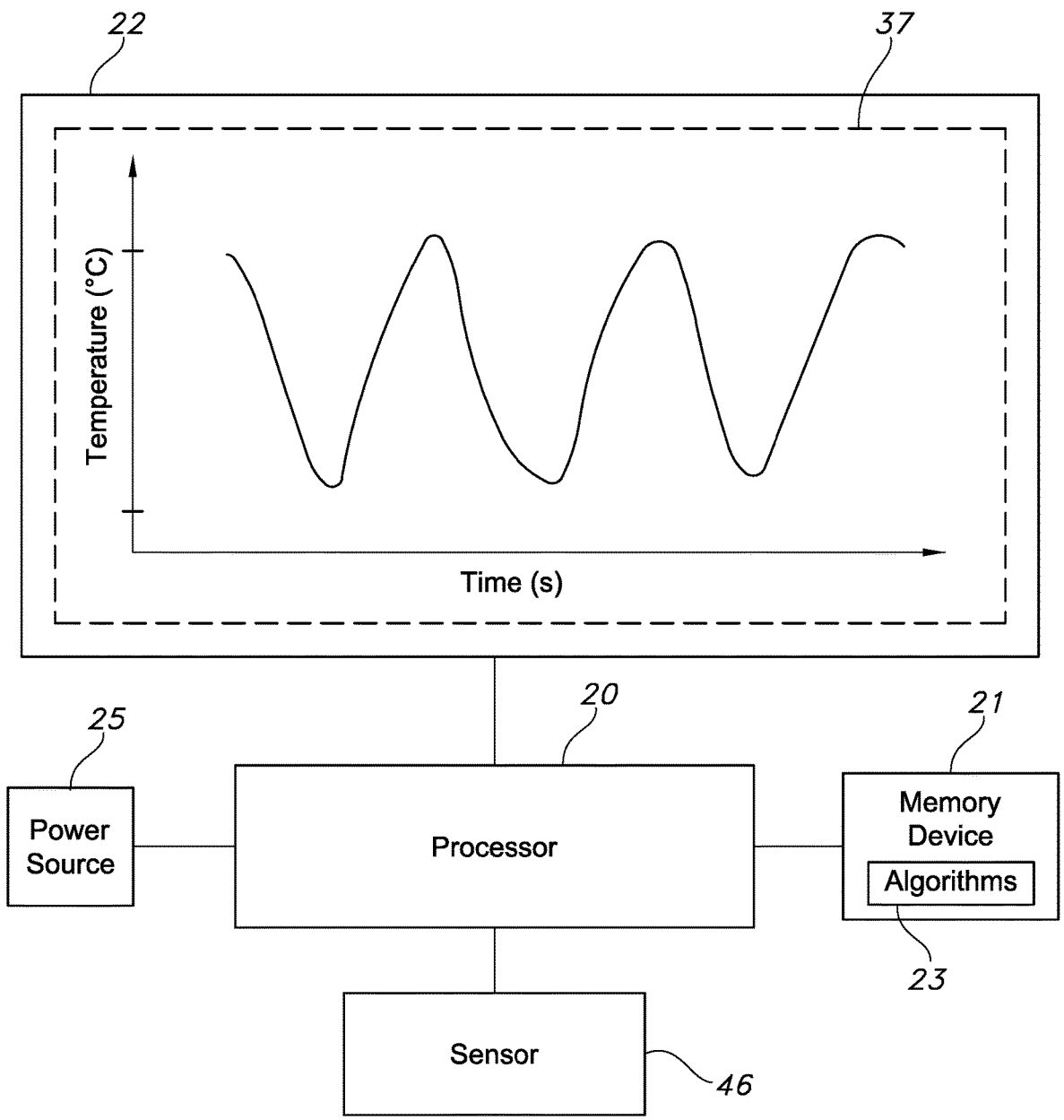
FIG. 8C is a schematic view of the catheter guidance system of the present invention as the system measures the temperature of air sampled from the catheter of FIG. 8A in real-time via the sensor assembly.

On the other hand, as shown in FIGS. 8A, 8B, and 8C, when the distal end or tip 60 of the catheter 50 is inserted into the nostril 87 of the patient and is advanced through the nasal cavity 88, past the nasopharynx 89, and into the trachea 92 just past the epiglottis 90, and then into the bronchi 93 or lungs 94, as the sensor 46 is continuously sampling air from the lumen of the catheter 50 over time in seconds (whether the sensor 46 is in the lumen 80 of the catheter 50 itself or in an air sampling chamber 54 as shown in FIGS. 1 and 4), the relative humidity (FIG. 7B) and temperature (FIG. 7C) graphs displayed or otherwise communicated by the processor 20, such as via the display device 22, show non-constant readings over time as the distal end or tip 60 of the catheter 50 travels into the respiratory system. With insertion of the catheter 50 inaccurately into the respiratory system, constant relative humidity and temperature readings are not obtained and this will ultimately be apparent to the health care provider within a matter of seconds of the insertion procedure once the distal end or tip 60 reaches the trachea 92, the bronchi 93, or the lungs 94, as the distal end or tip 60 of the catheter will be exposed to the pattern of breathing associated with inspiration and expiration, where the temperature and relative humidity levels rise and fall in a repetitive pattern and do not reach constant levels. At this point, the health care provider can be alerted to remove the tubing assembly 14 from the respiratory system and start a new procedure to accurately place the distal end or tip 60 of the catheter 50 into the digestive tract for enteral feeding.

Further, as an alternative or in addition to monitoring the temperature and/or relative humidity readings as determined by the sensor 46 over time and observing the change from non-constant or oscillating readings to constant readings, the health care provider can also verify accurate placement of the catheter 50 in the esophagus 91 rather than the trachea 92 by observing for the presence or absence of a plurality of markings 112 uniformly spaced along the external surface of the catheter. As described above, such markings 112 can be used in conjunction with the sensor 46 to determine accurate placement of the catheter 50. These markings 112 can function as placement markers which assist the user in assessing the depth that the catheter 50 is placed within the body 78. For instance, when the sensor 46 is located at the distal end 60 of the catheter 50, the markings 112 can be present from the distal end 60 of the catheter 50 to a point 126 on the catheter 50 that spans a distance that can correspond with the average distance between the trachea 92 and nostril 87 in a typical patient. As the catheter 50 is being inserted into the body 78 via the nostril 87, once the markings 112 are no longer visible outside the body 78, the health care provider can start looking for a constant temperature and/or relative humidity as measured by the sensor 46. If the temperature and/or relative humidity readings are still oscillating to the analog of breathing once the markings 112 are no longer visible outside the body 78, then the health care provider will know that the catheter 50 has been improperly inserted into the trachea 92 instead of the esophagus 91, and the catheter 50 can be immediately retracted.

Regardless of the particular method by which proper placement of the catheter 50 is determined, once the distal end or tip 60 of the catheter 50 has been accurately placed within the desired location in the digestive tract, the health care provider can then optionally remove the sensor 46, particularly when the sensor 46 is located within the lumen 70 of the catheter and includes a wired connection, where the wire assembly 62 electrically connects the sensor 46 to the processor 20 via the electrical connector or controller coupler 36, while the position of the catheter 50 is maintained. The health care provider can then attach medicine and nutritional delivery tubes to the y-port connector 44 for introducing fluids into the body (e.g., digestive tract) for medical treatment. On the other hand, if the sensor 46 is wireless or is placed within the air sampling chamber 54, the sensor 46 can optionally be left in place, and the health care provider can then attach medicine and nutritional delivery tubes to the y-port connector 44 for introducing fluids into the body (e.g., digestive tract) for medical treatment.

It should also be appreciated that the tubing assembly, electronic catheter unit and catheter position guidance system of the present invention can be used in a variety of catheter procedures and applications. These procedures may involve the treatment of the digestive or gastrointestinal tract or other portions of the human body. These procedures may involve treatment of humans by physicians, physician assistants, nurses or other health care providers. In addition, these procedures may involve treatment of other mammals and animals by veterinarians, researchers and others.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A tubing assembly comprising:
   a catheter having a proximal end, a distal end, and a tip, the catheter extending in a longitudinal direction, wherein the proximal end and the distal end define a lumen therebetween, and wherein the catheter is configured for placement within a digestive tract of a patient;
   an aspiration device;
   a first aspiration line;
   a second aspiration line;
   an air sampling chamber, wherein the air sampling chamber is connected to the first aspiration line;
   a sensor, wherein the sensor comprises a temperature sensor, a relative humidity sensor, or a combination thereof, wherein the sensor is located within the air sampling chamber;
   a filter disposed between the air sampling chamber and the first aspiration line capable of preventing liquid from contacting the sensor while allowing humid air to penetrate into the air sampling chamber;
   a multi-port connector including a nutrient branch, a medicine branch, and a catheter branch;
   a controller coupler or an electrical connector is-connected to the medicine branch; and
   an electrical tubular insulator comprising a tube having a proximal end attached to an attachment member of the controller coupler or the electrical connector;
   wherein the second aspiration line connects the aspiration device to the nutrient branch;
   wherein the first aspiration line connects the aspiration device to the electrical tubular insulator;
   wherein the proximal end of the catheter is attached to the catheter branch; and
   wherein the aspiration device is configured to draw air through the tubing assembly to expose the sensor to a continuous flow of air.

2. The tubing assembly of claim 1, wherein the sensor is configured to provide temperature readings, relative humidity readings, or a combination thereof measured by the sensor from air in the lumen to a processor in real-time.

3. The tubing assembly of claim 2, wherein the sensor is configured for a wired connection or a wireless connection to the processor.

4. The tubing assembly of claim 1, wherein the electrical tubular insulator surrounds a wire assembly, the wire assembly being connected between the sensor and a processor.

5. The tubing assembly of claim 1, wherein the air sampling chamber is connected to the first aspiration line via a connector in a sidewall of the first aspiration line.

6. A catheter guidance system comprising:
(a) a processor;
(b) a power source;
(c) a display device; and
(d) a tubing assembly comprising:
a catheter having a proximal end, a distal end, and a tip, the catheter extending in a longitudinal direction, wherein the proximal end and the distal end define a lumen therebetween;
an aspiration device;
a first aspiration line;
a second aspiration line;
an air sampling chamber, wherein the air sampling chamber is connected to the first aspiration line;
a sensor, wherein the sensor comprises a temperature sensor, a relative humidity sensor, or a combination thereof, wherein the sensor is located within the air sampling chamber;
a filter disposed between the air sampling chamber and the first aspiration line capable of preventing liquid from contacting the sensor while allowing humid air to penetrate into the air sampling chamber;
a multi-port connector including a nutrient branch, a medicine branch, and a catheter branch;
a controller coupler or an electrical connector is connected to the medicine branch; and
an electrical tubular insulator comprising a tube having a proximal end attached to an attachment member of the controller coupler or the electrical connector;
wherein the second aspiration line connects the aspiration device to the nutrient branch;
wherein the first aspiration line connects the aspiration device to the electrical tubular insulator;
wherein the proximal end of the catheter is attached to the catheter branch; and
wherein the aspiration device is configured to draw air through the tubing assembly to expose the sensor to a continuous flow of air;
wherein the sensor communicates with the processor via an electrical connection to deliver temperature readings, relative humidity readings, or a combination thereof measured by the sensor from air in the lumen to the processor in real-time;
wherein the display device is coupled to the processor and displays the temperature readings, the relative humidity readings, or the combination thereof communicated by the sensor;
wherein a constant temperature profile, a constant relative humidity profile, or both a constant temperature profile and a constant relative humidity profile after a pre-determined amount of time as shown on the display device indicates placement of the catheter in a digestive tract of a patient.

7. The catheter guidance system of claim 6, further comprising a memory device storing instructions which, when executed by the processor, cause the processor to (i) interpret the temperature readings, the relative humidity readings, or the combination thereof communicated by the sensor and (ii) cause the display device to communicate whether or not the catheter is placed within the digestive tract of the patient based on the interpretation of the temperature readings, the relative humidity readings, or the combination thereof.

8. A method for determining if a catheter is placed within a digestive tract of a body of a patient, the method comprising:
(a) inserting a distal end of a tubing assembly into an orifice of the body, wherein the tubing assembly comprises:
the catheter, wherein the catheter has a proximal end, a distal end, and a tip, wherein the catheter extends in a longitudinal direction, wherein the proximal end and the distal end define a lumen therebetween;
an aspiration device;
a first aspiration line;
a second aspiration line;
an air sampling chamber, wherein the air sampling chamber is connected to the first aspiration line;
a sensor, wherein the sensor comprises a temperature sensor, a relative humidity sensor, or a combination thereof, wherein the sensor is located within the air sampling chamber;
a filter disposed between the air sampling chamber and the first aspiration line capable of preventing liquid from contacting the sensor while allowing humid air to penetrate into the air sampling chamber;
a multi-port connector including a nutrient branch, a medicine branch, and a catheter branch;
a controller coupler or an electrical connector connected to the medicine branch; and
an electrical tubular insulator comprising a tube having a proximal end attached to an attachment member of the controller coupler or the electrical connector;
wherein the second aspiration line connects the aspiration device to the nutrient branch;
wherein the first aspiration line connects the aspiration device to the electrical tubular insulator;
wherein the proximal end of the catheter is attached to the catheter branch; and
wherein the aspiration device is configured to draw air through the tubing assembly to expose the sensor to a continuous flow of air;
(b) electrically connecting the sensor to a processor via a wired connection or a wireless connection;
(c) activating the sensor, wherein the sensor measures the temperature, the relative humidity, or the combination thereof from air in the lumen and communicates with the processor via the wired connection or the wireless connection to deliver temperature readings, relative humidity readings, or a combination thereof to the processor in real-time, wherein a display device is coupled to the processor and displays the temperature readings, the relative humidity readings, or the combination thereof communicated by the sensor;
(d) advancing the distal end of the catheter inside the body in a direction away from the orifice while the sensor is activated; and
(e) observing the temperature readings, the relative humidity readings, or the combination thereof on the display device, wherein a constant temperature profile, a constant relative humidity profile, or both a constant temperature profile and a constant relative humidity profile after a pre-determined amount of time indicates placement of the catheter in the digestive tract of the patient.

9. The method of claim 8, wherein a memory device stores instructions which, when executed by the processor, cause the processor to (i) interpret the temperature readings, the relative humidity readings, or the combination thereof communicated by the sensor and (ii) cause the display device to communicate whether or not the catheter is placed within the digestive tract of the patient based on the interpretation of the temperature readings, the relative humidity readings, or the combination thereof.

10. The method of claim 8, wherein the orifice is a nose or a mouth.

11. The method of claim 8, wherein suction from the aspiration device directs air sampled from the distal end of the catheter to the sensor.

* * * * *

UNITED STATES PATENT AND TRADEMARK OFFICE
CERTIFICATE OF CORRECTION

| | | |
|---|---|---|
| PATENT NO. | : 12,350,238 B2 | Page 1 of 1 |
| APPLICATION NO. | : 16/364362 | |
| DATED | : July 8, 2025 | |
| INVENTOR(S) | : Vernon Meadows et al. | |

It is certified that error appears in the above-identified patent and that said Letters Patent is hereby corrected as shown below:

On the Title Page

Item (56), Column 2, Line 1, delete "Report" and insert -- International Search --

In the Claims

Column 14, Lines 47-48, in Claim 1, delete "is-connected" and insert -- connected --

Signed and Sealed this
Twenty-third Day of September, 2025

John A. Squires
*Director of the United States Patent and Trademark Office*